United States Patent [19]

Carter

[11] Patent Number: 5,110,365
[45] Date of Patent: * May 5, 1992

[54] CONTROL OF FURNACE CLEANING FOR REFLECTIVE ASH USING INFRARED IMAGING

[75] Inventor: Hudson R. Carter, Granville, Ohio

[73] Assignee: The Babcock & Wilcox Company, New Orleans, La.

[*] Notice: The portion of the term of this patent subsequent to Mar. 17, 2009 has been disclaimed.

[21] Appl. No.: 621,417

[22] Filed: Dec. 3, 1990

[51] Int. Cl.$^5$ .......................... B08B 7/04; B08B 9/00; C21B 7/24; G01J 1/14
[52] U.S. Cl. ..................................... 134/18; 134/22.1; 134/113; 250/330; 250/342; 266/81; 266/90; 266/91
[58] Field of Search ................. 134/1, 18, 34, 37, 113, 134/22.1; 266/81, 90, 91; 250/330, 342

[56] References Cited

U.S. PATENT DOCUMENTS

| | | | |
|---|---|---|---|
| 2,200,668 | 5/1940 | Carlson | 134/22.1 |
| 3,588,067 | 6/1971 | Mori et al. | 266/90 |
| 3,782,336 | 7/1974 | Nelson | 122/379 |
| 4,209,028 | 3/1980 | Shenker | 134/56 R |
| 4,644,173 | 11/1987 | Jeffers | 250/554 |
| 4,690,634 | 3/1987 | Herngren et al. | 431/8 |

OTHER PUBLICATIONS

Water Cleaning Performance Evaluations, Nebraska Public Power District, Gerald Gentleman Station, Final Report, Nov. 12, 1990.
"Flame Quality Analyzer for Temperature Measurement and Combustion Control", SENSORS, vol. 5, Jan. 1988.
On-Line Imaging and Emissivity Measurements to Determine Furnace Cleanliness, H. R. Carter and C. G. Koksal, draft copy of paper to be presented in Oct. 1991.
Cost and Quality of Steam Coal Deliveries, Producing State/Consuming State, "Power Plant Deliveries, Data for Feb. 1991", from National Coal Association, May 1991 issue.
"Reflectivity/Emissivity Character of Western Fuel", Clark, Gregory A., Alliance Research Center 1990, Western Fuels Conference, Sep. 11, 1990, Minneapolis, MN.
"Measurement of Radiactive Properties of Ash and Slag by FT-IR Emission and Reflection Spectroscopy", Solomon, Peter et al., submitted to Journal Heat Transfer 1991.
"Monitoring of Recovery Boiler Interiors Using Imaging Technology" Anderson, Marc J. et al., CPPA-- TAPPI 1989 International Chemical Recovery Confernce.
Promotional Brochure Advertisement.
"Flame Quality Analyzer for Temperature Measurement and Combustion Control", R. T. Bailey and H. R. Carter.

Primary Examiner—Theodore Morris
Assistant Examiner—Saeed Chaudhry
Attorney, Agent, or Firm—Vytas R. Matas; Robert J. Edwards; Daniel S. Kalka

[57] ABSTRACT

A method and apparatus for monitoring reflective ash deposited on a furnace wall to be cleaned, comprises an infrared video camera or other mechanism for taking an infrared image of the furnace wall. The image must include an area to be cleaned by the waterblowing as well as a surrounding uncleaned area. Photo detectors or other mechanisms are utilized to measure the image intensity at locations on the cleaned and uncleaned areas with a ratio between the intensities being taken. The cleaned area has low reflectivity and is dark compared to the uncleaned area which is white and has high image intensity. The image intensity ratio between the cleaned area and the uncleaned area thus rises from a low level immediately after waterblowing to a high level which approaches unity as the initially cleaned area becomes as unclean as the uncleaned area. This can be used as an indication when waterblowing must be manually initiated, or the ratio signal can be used directly to operate an automatic system to initiate waterblowing.

15 Claims, 1 Drawing Sheet

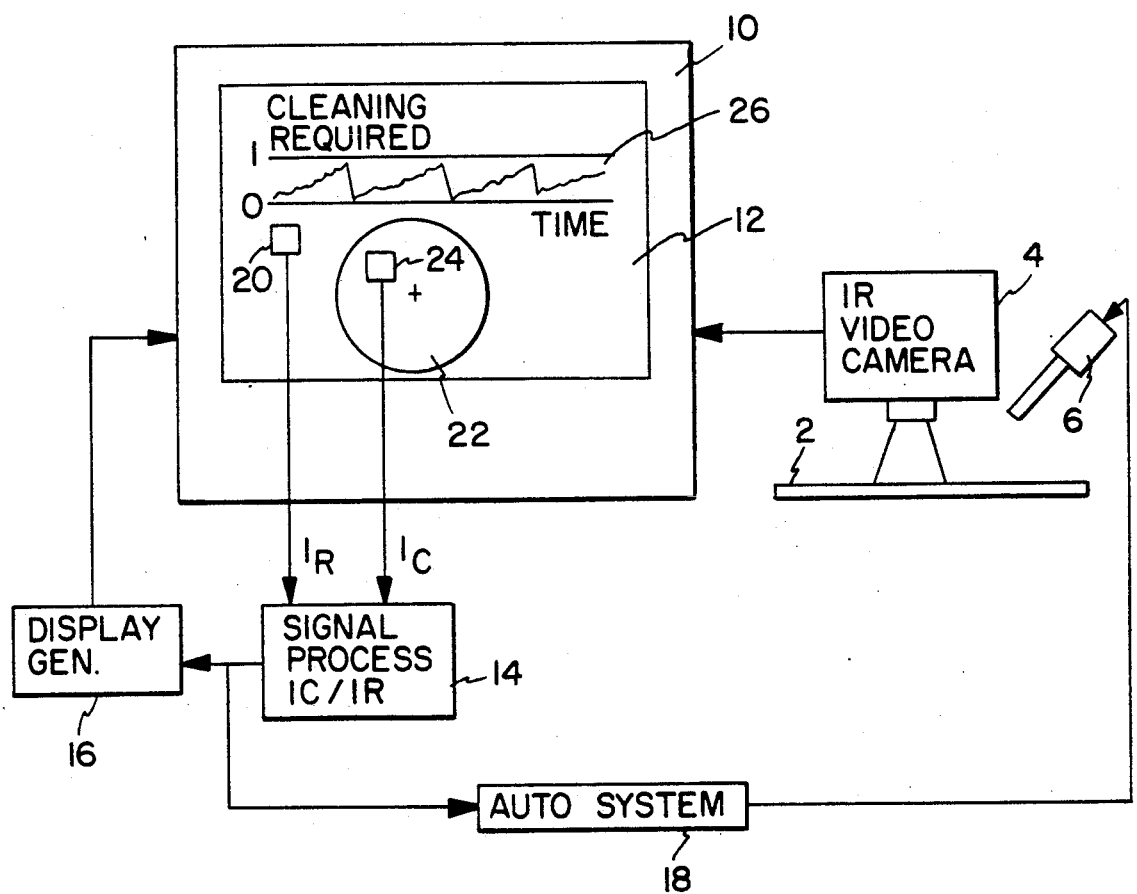

CONTROL OF FURNACE CLEANING FOR REFLECTIVE ASH USING INFRARED IMAGING

FIELD AND BACKGROUND OF THE INVENTION

The present invention relates in general to monitors for use in furnaces and other high temperature, dirty environments, and in particular to a new and useful monitor which is capable of determining the cleanliness of a furnace wall that receives deposits of highly reflective ash.

Western fuels, such as Powder River Basin (PRB) coals, are low in sulfur; however, they are high in calcium and silicon. This composition results in a thin, white tenacious ash on the furnace walls. This ash (called slag) is not easily removed using conventional air or steam cleaning devices.

A number of utilities are currently burning PRB coal and more are expected to switch to PRB coal with the passage of the Clean Air Act. The PRB coal deposited ash is highly reflective. The ash reduces the heat absorption of the furnace causing high temperatures in the convection passes of the boiler.

Waterblowing has been shown to be effective in removing the ash and restoring furnace heat transfer effectiveness. More utilities are expected to employ waterblowing when PRB coal is used.

The PRB ash deposit is thin and tight. This is in stark contrast to the heavy deposits visually apparent in furnaces burning other coals. Therefore, the decision to clean the furnace cannot be made based on a visual inspection and overcleaning (with water) is not desired because of thermal shock consideration.

Since there is a thermal shock consideration in using water, it is desirable to only clean the wall when cleaning is necessary. All plants currently clean on a time sequence. Most plants use a cleaning period of about four hours. Video recording taken at one plant reveals that for the hot wall (this was a tangentially fired boiler) four hours was an appropriate time period. However, on the cold wall a much longer period than four hours should be used. Based on the video recording even after ten hours the cold wall was still relatively clean.

A need thus exists for apparatus and techniques which are capable of accurately distinguishing between a clean condition for the furnace wall which does not require immediate waterblowing, and an unclean condition which does require waterblowing.

SUMMARY OF THE INVENTION

The present invention is based on the discovery that an infrared picture taken of a furnace wall, shows that clean surfaces appear nearly black while slag covered surfaces are white. In the near-infrared region (approximately 1.5 to 2.1 microns) the image viewed is a temperature image. Therefore the black or dark area is cooler than the white area. The clean surfaces are cooler than the dirty surfaces because the clean surfaces are closer to the inside diameter of the coolant flow in the furnace wall. Therefore, the cooler surfaces are the cleaner, and thus darker, surfaces.

To apply this discovery, a measurement is taken of the intensity ratio between a known cleaned area of the furnace wall as viewed on a video image screen, and an area which has not been cleaned. As this ratio approaches 1 (indicating that the cleaned area is no longer clean) waterblowing steam blowing or airblowing, or combinations thereof are instituted by activating cleaning equipment of known design. Since the equipment produces a clean area of known extent, the distinction between the intensity of the cleaned area and the intensity of an uncleaned area (which is never reached by the water lance) is readily made.

An infrared video image can be produced using the known infrared monitoring equipment disclosed in U.S. Pat. No. 4,539,588 (which is incorporated here reference). This equipment or conventional photodetection equipment can be used for measuring the intensities of the clean area and reference area and conventional calculating equipment utilized to establish the ratio.

Accordingly, an object of the present invention is to provide a method of monitoring for high reflectivity ash deposited on a furnace wall which has at least one area to be cleaned by waterblowing and a remaining uncleaned reference area, comprising: taking a near infrared image of the wall including the cleaned area and the uncleaned reference area; measuring image intensity at a location on the cleaned area; measuring image intensity at a location on the reference area; and determining the ratio between the image intensities of the cleaned and reference areas as a measurement of the amount of high reflectivity ash deposited on the furnace wall.

A further object of the present invention is to provide an apparatus for monitoring the furnace wall.

A still further object of the present invention is to provide a method and apparatus for monitoring the furnace wall which is simple in design, rugged in construction and economical to manufacture.

BRIEF DESCRIPTION OF THE DRAWING

The only figure in the drawing is a schematic representation of the apparatus of the present invention.

DESCRIPTION OF THE PREFERRED EMBODIMENT

Referring to the drawing in particular, the invention embodied therein comprises an infrared camera 4 for viewing a near infrared image of a furnace wall 2 which is to be periodically cleaned by a water lance 6. The video camera is connected to a monitor 10 which has a screen 12 which, at its lower half, displays the furnace wall which includes an area 22 which is expected to be cleaned by the water lance 6, and a remaining reference area around the cleaned area 22, which is not expected to be cleaned by the waterblowing operation. A first photo detector 20 is positioned at a location in the uncleaned reference area while a second photo detector 24 is positioned at a location in the clean area 22. Alternately, a single infrared camera may be used to monitor both locations. It is expected that immediately the cleaning operation, the cleaned area 22 will be dark or black while the uncleaned surrounding area will be white or highly reflective. The intensities of the two areas are supplied as signals to a signal processor 14 which takes the ratio between the clean area intensity $I_c$ and the reference area intensity $I_R$ to drive a display generator 16 which produces a display 26 at the upper half of screen 12. Display 26 is in the form of a graph which plots the ratio of $I_C/I_R$ over time. The gradually increasing slope of the repeating pattern represents the slow deposition of reflective ash on the furnace wall 2. Since the intensity of area 22 is initially very low while the intensity of the dirty area at location 20 is substantially constant and relatively high, the value on display 26 increases from near 0 to near 1 as ash is deposited. When the cleaned area is nearly as reflective as the uncleaned area, this indicates a point when waterblowing must be initiated. At that point, a rapid cleaning takes place which results in a rapid decrease in the ratio as shown in display 26.

The signal from signal processor 14 may also be used to drive an automatic WL activation system 18 which activates the water lance 16 when the selected peak values for the ratio (near unity) is reached on a periodic basis.

Although a single clean area 22 is illustrated, it is understood that several water lances may be used in a pattern which is preferably non-overlapping. The non-overlapping nature of the generally circular patterns is selected since the overlapping areas (which are cleaned by two water lances) would be subjected to excessive thermal shock.

The use of the invention also avoids excessive and unnecessary cleaning which not only saves energy and wear on the WL system, but also reduces thermal shock to the furnace walls.

Although a real-time video monitor 10 is illustrated, snap shots or other static images may be generated using the video camera 4. Alternatively, an array of near infrared sensors may be utilized to generate the image or any other infrared image system may be utilized.

Photo detectors 20 and 24 may be replaced by any other mechanism which is capable of detecting intensity in the image.

Actual tests that have been conducted on at least one power generating station have verified the usefulness and applicability of the present invention to monitor and control waterblowing operations.

While a specific embodiment of the invention has been shown and described in detail to illustrate the application of the principles of the invention, it will be understood that the invention may be embodied otherwise without departing from such principles.

What is claimed is:

1. A method for controlling periodic furnace wall cleaning by distinguishing between a clean condition for a furnace wall from an unclean condition for high reflectivity ash deposited on the furnace wall which has at least one area to be cleaned and a remaining uncleaned reference area, comprising the steps of:
   taking a near infrared image of the furnace wall including the area to be cleaned and the uncleaned reference area;
   measurings image intensity at a location on the area to be cleaned and establishing a signal indicative thereof;
   measuring image intensity at a location on the uncleaned reference area and establishing a signal indicative thereof;
   supplying the image intensity signals to a signal processor for determining a ratio between the image intensities of the area to be cleaned and reference area;
   comparing the ratio of the image intensities with a selected value for distinguishing an unclean condition for the furnace wall from a clean condition; and
   initiating furnace wall cleaning when the ratio reaches the selected value indicating the unclean condition of the furnace wall.

2. A method according to claim 1 including utilizing an infrared video camera to take the image and to measure the image intensity at the locations of the cleaned and reference areas.

3. A method according to claim 1 including displaying the ratio as it changes as a function to time to indicate the increase of reflectivity in the cleaned area corresponding to an ever increasing deposit of ash.

4. A method according to claim 1 including measuring a selected peak of the ratio and utilizing the peak to control the initiation of a waterblowing operation to clean the cleaned area.

5. A method according to claim 1, wherein the furnace wall cleaning includes steam blowing.

6. A method according to claim 1, wherein the furnace wall cleaning includes air blowing.

7. A method according to claim 1, wherein the furnace wall cleaning includes water blowing.

8. An apparatus for controlling periodic furnace cleaning by distinguishing a clean condition for a furnace wall from an unclean condition by monitoring high reflectivity ash deposited on the furnace wall having at least one area to be cleaned and a remaining uncleaned reference area, comprising:
   means for generating a near infrared image of the wall including the area to be cleaned and the uncleaned reference area;
   means for measuring the image intensity at a location in the area to be cleaned and establishing a signal indicative thereof;
   means for measuring the image intensity at a location in the uncleaned reference area and establishing a signal indicative thereof; and
   a signal processor receiving the image intensity signals to calculate a ratio between the image intensities which represents a measurement of the furnace wall ash deposit on the area of the furnace wall to be cleaned, said signal processor comparing the ratio with a selected value for distinguishing an unclean condition from a clean condition of the furnace wall, said signal processor providing an output signal indicative of the unclean condition on the furnace wall when the ratio reaches the selected value.

9. An apparatus according to claim 8, wherein said means for providing the near infrared image comprises an infrared camera for imaging the furnace wall.

10. An apparatus according to claim 8, wherein the means for measuring the image intensity comprise photo detectors positioned over the respective locations on the infrared image.

11. An apparatus according to claim 8 including automatic means for connection to a cleaning mechanism, said automatic means being connected to the signal processor and being responsive to said output signal for being activated when the ratio reaches the selected value.

12. An apparatus according to claim 11, wherein the cleaning mechanism comprises water blowing equipment.

13. An apparatus according to claim 11, wherein the cleaning mechanism comprises steam blowing equipment.

14. An apparatus according to claim 11, wherein the cleaning mechanism comprises air blowing equipment.

15. An apparatus according to claim 8, wherein said signal processor displays the ratio on a display as it changes as a function of time to indicate the increase of reflectivity in the cleaned area corresponding to an ever increasing deposit of ash.

* * * * *